United States Patent [19]
Covington et al.

[11] Patent Number: 5,368,578
[45] Date of Patent: Nov. 29, 1994

[54] HYPODERMIC SYRINGE HOLDER

[75] Inventors: Roger G. Covington; Karen A. Malburne, both of Rochester, N.Y.; Douglas C. Mehl, Columbus, Ohio; John Niedospial, Princeton Junction, N.J.

[73] Assignee: Sterling Winthrop Inc., New York, N.Y.

[21] Appl. No.: 209,583

[22] Filed: Mar. 10, 1994

[51] Int. Cl.⁵ .............................................. A61M 5/00
[52] U.S. Cl. ....................................... 604/232; 604/187
[58] Field of Search ............... 604/232, 233, 187, 218, 604/264

[56] References Cited

U.S. PATENT DOCUMENTS

| | | | |
|---|---|---|---|
| 2,228,537 | 1/1941 | Smith | 604/233 X |
| 2,871,858 | 2/1959 | Dann et al. | 604/233 |
| 4,594,073 | 6/1986 | Stine | 604/232 X |
| 4,787,891 | 11/1988 | Levin et al. | 604/187 X |
| 5,176,657 | 1/1993 | Shields | 604/232 |

Primary Examiner—John D. Yasko
Attorney, Agent, or Firm—Gilbert W. Rudman

[57] ABSTRACT

A hypodermic syringe holder adapted to receive a disposable ampoule and eject it in an axial direction. The holder comprises a plunger element, an optional camming element, a disposable hollow semi-cylindrical frame and a forwardly pivotable element.

7 Claims, 5 Drawing Sheets

HYPODERMIC SYRINGE HOLDER

BACKGROUND OF THE INVENTION

1. Field of the Invention

This invention relates to the field of hypodermic syringe holders for use in combination with disposable medicament-containing ampoules.

2. Description of the Prior Art

Disposable medicament-containing cartridge-needle units for use in conjunction with hypodermic syringe holders are well known in the art. Such cartridges conventionally feature a cylindrical body closed at the proximal end worth a flexible piston slidable within the bore of the cartridge and closed at the distal necked-down end with a diaphragm secured to the cartridge by a crimped-on metal collar. The necked-down distal end conventionally is fitted with a steel needle/needle hub unit and a needle sheath. Such needle/needle hub units have, minimally, a sharp end, typical of the type associated with hypodermic syringes.

Such cartridge-needle units can be used in conjunction with syringe holders which allow the user to avoid handling the cartridge-needle unit when the needle is exposed. Nevertheless, health care workers are especially susceptible to accidental and potentially infectious, and indeed, on occasion, possibly fatal, needle strikes due to careless handling and/or disposal of the cartridge-needle unit after use. The consequences to health care workers of strikes from needles contaminated with various infectious diseases such as hepatitis or AIDS can be particularly severe. The frequency of such accidental needle strikes in the United States is surprisingly great, and has been estimated to be approximately one million needle strikes per year. However, the cost to health care organizations for the testing of health care workers accidentally stricken by used needles is a significant burden on health care costs. Therefore, it would be desirable to further protect health care workers by providing medicament-containing cartridges without having to expose the user to the needle commonly associated with such cartridges.

In response to the "accidental needle strike" situation, numerous devices have been developed which allow the spent disposable medicament-containing ampoules to be removed from the holder without handling by the health care worker.

EPO case 0485028A1 describes a readily assembled, snap together hypodermic syringe holder. The body of the holder is a semi-cylindrical body. When the ampoule is to be ejected, the semi-cylindrical is positioned so its open side is faced downward. Gravity forces permit the ampoule to fall. The problem with this holder is that occasionally the ampoule is caught altering the trajectory of the ampoule's fall. This altering of the trajectory may cause "accidental needle strikes".

U.S. Pat. No. 5,028,698 describes an axial eject hypodermic syringe holder. This holder has a pair of pivotable jaws at the needle end of the holder. When the medicament-containing ampoule is to be removed from the holder and dropped by gravity into a disposal unit, the jaws are opened sufficiently to allow the ampoule to slidingly eject from the holder. The problem with this holder is the amount of parts required.

It would be highly desirable to provide a holder having a simplified and improved construction which allows for axial ejection of the ampoules.

SUMMARY OF THE INVENTION

In accordance with this invention, there is provided an improved hypodermic syringe holder adapted to receive a disposable ampoule comprising (a) a plunger element, (b) a hollow body for receiving the disposable ampoule, and (c) optionally, a cammimg element.

The improvement is the body being comprised of a semi-cylindrical hollow frame and a forwardly pivotable element. The semi-cylindrical hollow frame has a distal end portion and a proximal end portion. The distal end portion of the frame has lugs on its outside surface radially positioned to pivotably engage a forwardly pivotable element, and has a projecting means on its inside surface to position the disposable ampoule. The proximal end portion of the frame has (a) a short cylindrical section with a bore therethrough for receiving the plunger element and the optional camming element, (b) a finger gripping means and (c) a projecting means on its inside surface to position the disposable ampoule or engage and position the optional camming means which then positions the disposable ampoule.

The forwardly pivotable element has two side walls joined by an extended connecting wall. The distal end of each side wall has a slot for inserting a lug of the distal end portion of the frame upon which the element can pivot. The connecting wall has a radial curved portion sized to continue the cylindrical shape of the frame when the forward pivotable element is in a closed position and a curved opening at the distal end thereof shaped to continue the cylindrical shape of the frame when the pivotable element is in an open position. The disposable ampoule can be ejected from the hollow semi-cylindrical frame in an axial direction through the curved opening when the pivotable element is in an opened position. Additionally, the forwardly pivotable element on its inside surface at the proximal end of the curved opening, has projections which are parallel to the side walls and adapted to engage, position and optionally activate the disposable ampoule when the pivotable element is in a closed position.

Embodiments of the invention use a plunger element including a rod portion having on its lower end a piston engaging means, the rod portion and piston engaging means being axially and slidably receivable within the bore of the camming element or bore of the short cylindrical section as required in the particular device. The piston engaging means is used to selectively attach the plunger element to the piston of the disposable ampoule.

In an embodiment of the invention which uses a camming element, the camming element is axially movable and rotatable about its longitudinal axis within the bore within the short cylindrical section of the proximal portion of the frame and engageable with an associated ampoule to securely immobilize the ampoule within the body portion of the syringe holder. In a preferred embodiment the camming element is comprised of a barrel portion, a handle portion, a helical groove on the outer surface of the barrel portion, a bore therethrough and ramp means connecting the helical groove with the lower surface of the camming element, the barrel portion being sized to rotate and translate within the cylindrical section of the hollow frame.

It is an advantageous feature of this invention that there is provided a syringe holder of simple construction, i.e., containing just three or four working parts, which can be easily and economically manufactured in large quantities, e.g., by injection molding techniques.

It is another advantageous feature of this invention that there is provided a syringe holder which can be readily assembled, i.e., by snapping together the hollow frame, forwardly pivotable element, plunger element and optional camming element.

Yet another advantageous feature of this invention is that there is provided a syringe holder readily adapted to immobilize a cartridge ampoule within the holder during use having manual aspirating capability.

Other advantages will become readily apparent upon reference to the following description of preferred embodiments when read in light of the accompanying drawings.

DESCRIPTION OF PREFERRED EMBODIMENTS

While this invention is described particularly with respect to a hypodermic syringe holder, it also finds utility in other holders adapted to dispense a fluid from a disposable cartridge.

As used herein, the terms "lower", "downward", and "distal" are intended to make reference to the end of the syringe or components thereof, which would be furthest from the health care worker holding the syringe during use (the most distal end of the syringe would be the needle point). Conversely, the terms "upper", "upward", and "proximal" are intended to make reference to the end of the syringe or components thereof which would be nearest to the health care worker during use (the most proximal end of the syringe would be the plunger actuation button).

Figure 1:
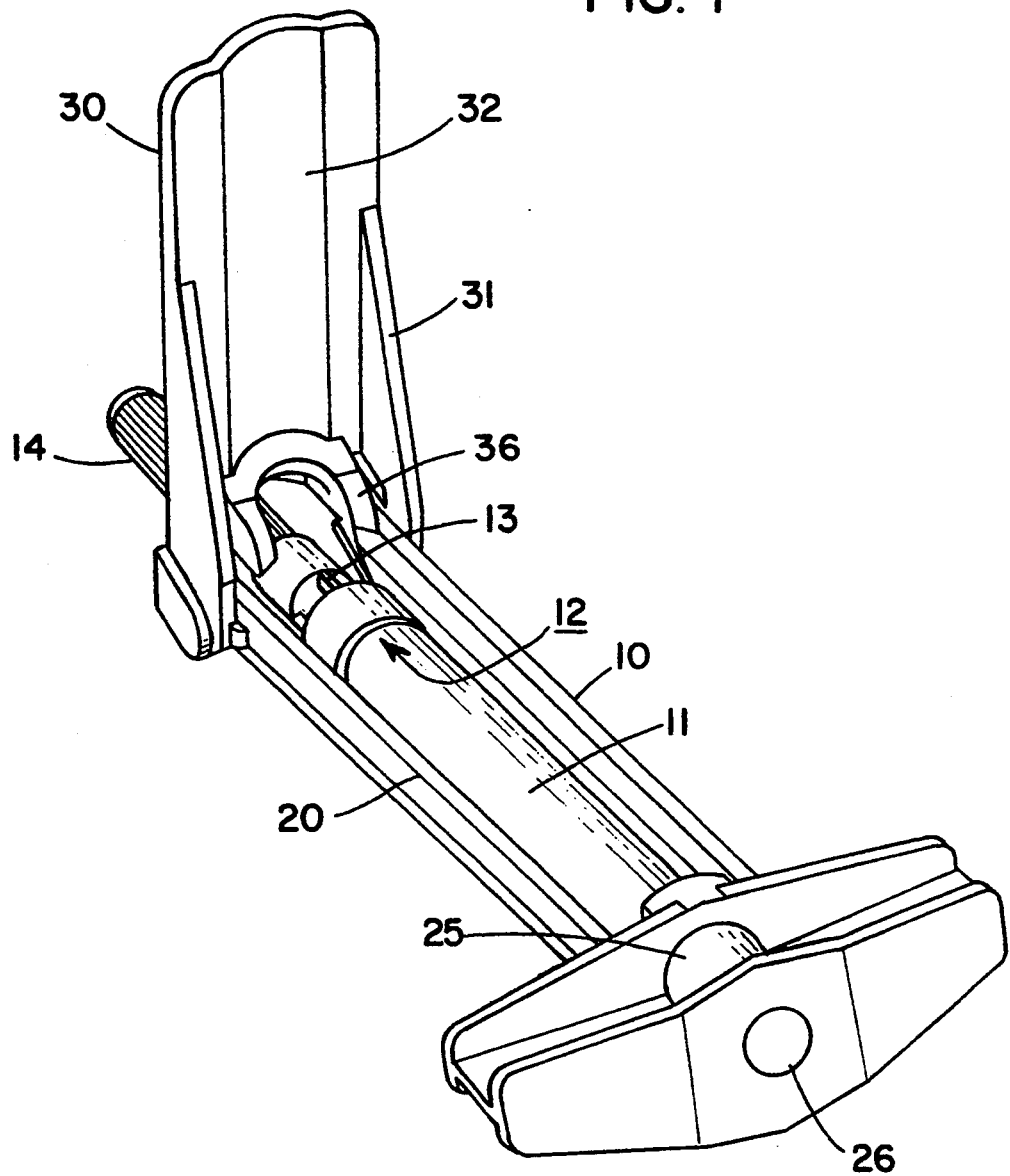
FIG. 1 is a perspective view of a syringe holder of the invention.

Referring to FIG. 1, the syringe holder of the invention 10, is intended for use in combination with conventional medicament-containing ampoule 11 which is closed at the upper end with a flexible piston slidable (not shown) within the bore of the ampoule and closed at the lower end by a rubber diaphragm secured to the ampoule by a crimped-on metal collar 12. The necked-down end is conventionally fitted with a needle/needle hub unit 13 and a needle sheath 14. A typical such ampoule/needle assembly is sold commercially as CARPUJECT ®.

Figure 4A:
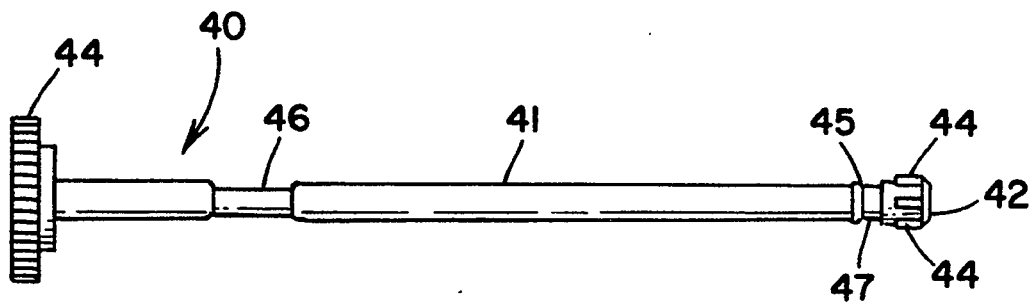
FIGS. 4A and 4B are plan and end views, respectively, of the plunger element of a syringe holder of the invention.
Figure 4B:
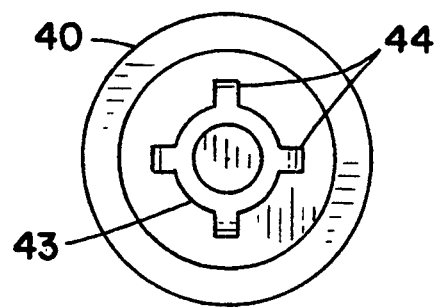

In the preferred embodiments the syringe holder comprises a total of three elements, namely, a generally semi-cylindrical arid hollow frame portion 20, a forwardly pivotable element 30, and a plunger element 40 shown in FIGS. 4A and 4B.

The hollow frame is sized to permit the ampoule to be placed into the body. A bore 26 is sized to receive the plunger element 40 or optionally the camming element 50 shown in FIGS. 5A–C.

The proximal portion of the hollow frame is provided on its inside surface with a projection 28, shown in FIG. 2B, used to position the ampoule or to attach and operationally act with the camming element which is described in further detail herein below.

The projection can conveniently be molded integrally with the frame, thus eliminating the need for additional molding and sealing of the projection to the frame.

Figure 2A:
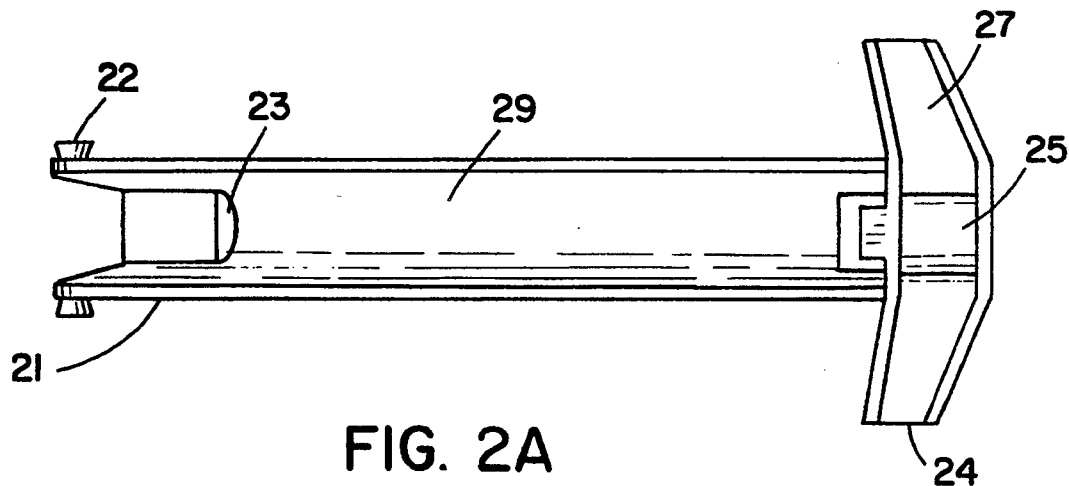
FIGS. 2A, 2B and 2C are a plan view, a side elevational view and a proximal end view, respectively, of a semi-cylindrical hollow frame of a preferred syringe holder of the invention.

The frame is equipped with another projection 23, shown in FIG. 2A, located near the distal end of the frame portion, which serves to align an ampoule within the body of the syringe holder with the tip of the piston engaging means 42, shown in FIG. 4A.

Figure 2B:
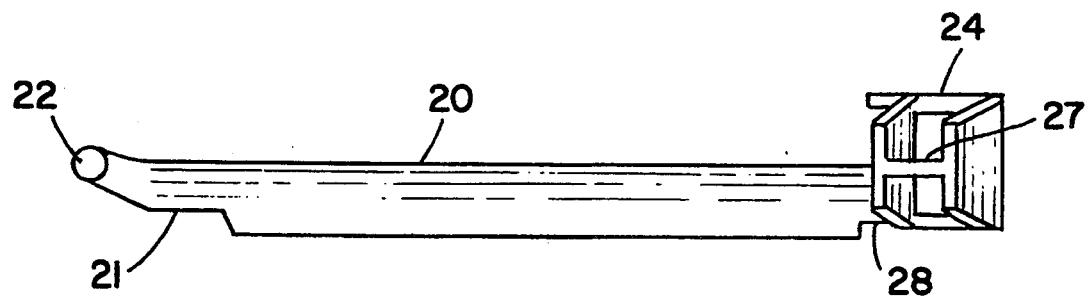
Figure 2C:
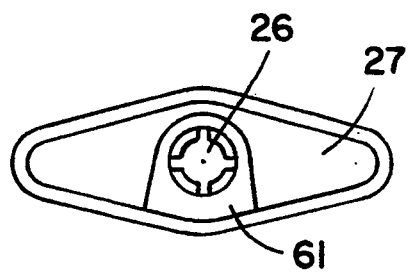

With reference to FIGS. 2A, 2B and 2C, a semi-cylindrical hollow frame 20 is comprised of a distal end portion 21 and a proximal end portion 24. The distal end portion has lugs 22 on its outside surface radially positioned to pivotably engage a forwardly pivotable element 30, and a projecting means 23 on its inside surface to position the disposable ampoule. The proximal end portion 24 has cylindrical section (in this embodiment incorporated within the finger gripping means 27) hayinc a bore 26 therethrough sized for receiving the plunger element 40 or optional camming element 50. The proximal end portion also has a a projecting means 28 on its inside surface to position the disposable ampoule or in an embodiment not shown to engage and position the camming means.

Figure 3A:
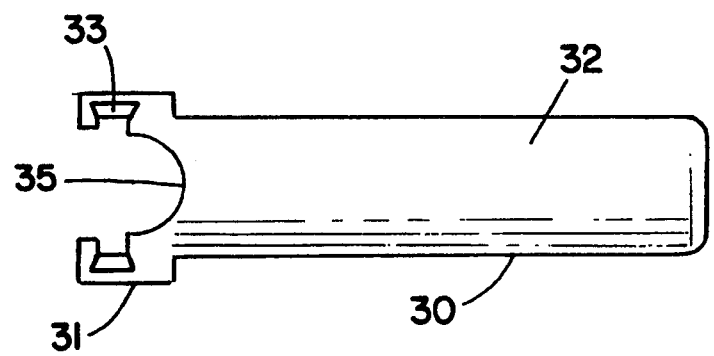
FIGS. 3A, 3B and 3C are a plan view, side view and distal end view, respectively, of the forwardly pivotable element of a preferred syringe holder of the invention.
Figure 3B:
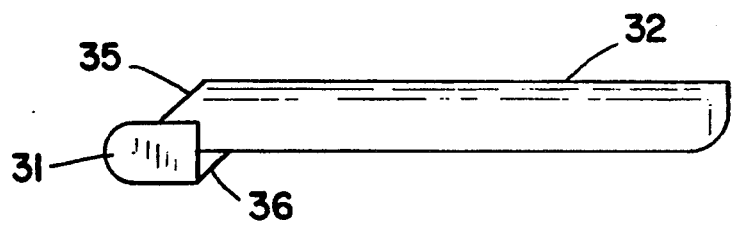
Figure 3C:
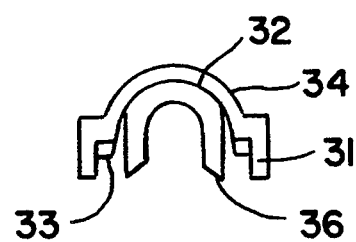

Referring to FIGS. 3A, 3B and 3C, the forwardly pivotable element 30 is comprised of two side walls 31 joined by an extended connecting wall 32. Each side wall 31 has a slots 33 inserting a lug 22 of the distal end portion of the frame upon which the element can pivot and which can frictionally attach the pivotable element and the hollow frame.

The connecting wall 32 has a radial portion 34 curved to continue the cylindrical shape of the frame when the forwardly pivotable element is in a closed position and a curved opening 35 at the distal end of the connecting wall to continue the cylindrical shape of the frame when the pivotable element is in an open position. The curved opening 35 is sized to allow the disposable ampoules to be ejected in an axial direction therethough when the pivotable element is in an open position. There are projections 36 on the inside surface at the proximal end of the curved rounded opening. The projections 36 are parallel to the side walls 31 and adapted to engage and position the disposable ampoule when the pivotable element is in a closed position.

Referring now to FIGS. 4A and 4B The plunger element 40 preferably consists of a unitary injection moldable structure. However, the piston engaging means 43 and/or the actuation button 44 may be affixed to the rod after the rod has been inserted through the bore of the camming element. The plunger element may have a shaft portion 41 and head portion 42.

Figure 5A:
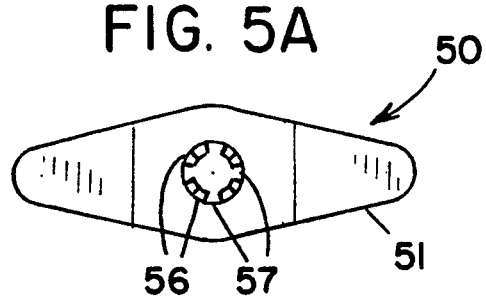
FIGS. 5A, 5B and 5C are a proximal end view, plan view and cross sectional view, respectively, of a optional camming element of a syringe holder of the invention.
Figure 5B:
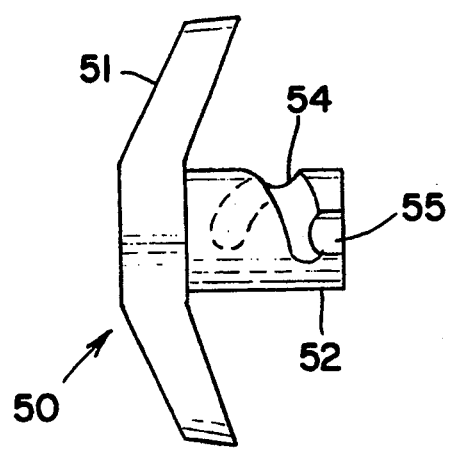
Figure 5C:
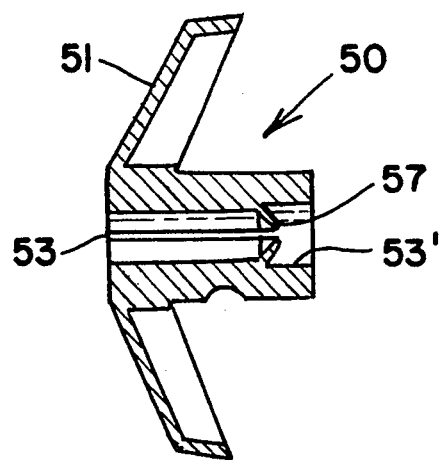

Referring now to FIGS. 5A, 5B, and 5C, the ampoule camming element consists of a pair of handles 51 and a barrel 52 having a relatively small diameter bore 53 sized to slidably receive at east the shaft 41, and preferably both the shaft and head portions 42 of plunger element 40. The barrel of camming element 50 has a slightly expanded bore section 53 which is sized to accept piston engaging means 43 and which has a slightly larger diameter than the shaft portion of the plunger. Extending partially around the outer surface of camming element 50 is a helical groove 54. Helical groove 54 is semi-circular in cross section and is of such width and depth as to slidably receive a hemispherical projection 28 positioned on the inside surface of the proximal portion of frame 20 when the camming element is appropriately inserted into the bore of the frame sized to receive the camming element.

The barrel portion of the camming element is provided with ramp means 55 connecting the distal part of helical groove 54 with the distal surface of the camming element. Helical groove 54 is slidably accessible to hemispherical projection 28 through ramp means 55 and engageable with the projection in such a manner so as to secure the camming element to the frame portion such that all the elements of the syringe holder are in cooperative engagement with one another.

In an embodiment of the invention, camming element 50 is provided with fingers 56 and grooves 51 on the inside diameter of bore 53, the distal portion of rod 41 is provided with fins 44, and the distal portion of rod 41 is provided with undercut means 57. When inserted through the bore, the fins travel through the grooves and the head of the rod is capable of flexing the fingers. The fingers are engageable with the undercut means to capture the plunger element in the camming element. The fins simulate a larger head diameter engageable which the ampoule which is desirable, while the smaller rod diameter reduces drag for aspiration and minimizes undesirable relaxation of the fingers, for example, that which can result during high temperature sterilization. Keying means 57 can be provided so that the fins align themselves with the grooves upon insertion of the distal portion of the plunger element into the bore. The rod can be provided with radial ribs 45 which retain the plunger rod in the rear position and aid in cartridge ejection, and detent means 46 which functions to minimize undesirable relaxation of the fingers.

As noted above, the various parts of the syringe holder can be readily assembled. For example, plunger element 40 can be inserted through the bore 26 of hollow frame 20 or bore 53 of the camming means 50 in a "one way" or "insert only" manner. If the optional camming means is utilized then a subassembly of the camming means/plunger means is then inserted into the proximal end of the bore 26 of the hollow frame 20. In this embodiment, the camming element is rotated so that the ramp means engages the projection, which is a hemispherical lug, on the inside surface of the hollow frame. The camming element is then pressed into the frame such that the hemispherical lug slides through the ramp means and acquires access to the helical groove. All the elements of the syringe holder are thereby joined together in cooperative relationship with one another.

In use, when the pivotable element is rotated into the open position, an ampoule/needle/needle hub/needle sheath unit is inserted into the hollow 29 of the frame. The pivotable element is then rotated into the closed position. The projections 36 position the ampoule/needle/needle hub/needle sheath unit and, in a preferred embodiment without a camming means, cause movement of the needle hub to activate the ampoule.

Although the various elements of the syringe holders described herein may be made of any suitable material including metals or plastics, they are well adapted to fabrication of plastic. In particular, hollow frame 20, pivoting element 30, optional camming element and plunger element 40 can be fabricated by known precision injection molding techniques. When the various elements are constructed of plastic, suitable plastics include high density polyethylene, polycarbonate, polystyrene, ABS (clear of opaque), nylon, acetals such as DELRIN ® or polypropylene. It is particularly advantageous that the body portion be fabricated of a transparent material so that the ampoule is visible during operation. The plastic preferably is injection moldable. As noted, a particularly advantageous feature of this invention is that the various pieces of the syringe holder, i.e., the frame, pivotable element, catching element and plunger element can be easily and economically manufactured in large quantities by known precision injection molding techniques. When the holder is intended for use in a high temperature sterilization process, the plastic preferably is substantially resistant to deformation at sterilization temperatures.

It will be appreciated that minor modifications in the various elements of the invention may be made without departing from the spirit of the invention. For example, the piston engaging means is described herein as being a screw-threaded element which mates with a screw-threaded post on the ampoule piston. Such means of engaging the plunger with the piston is a preferred means, however, other piston engaging means well known in the art, such as, for example, multiple retractable claws or hooks, fixed claws, an expandable chuck, resilient gripping fingers, a harpoon, or a bayonet connection will serve the purpose as well.

We claim:

1. An improvement in an hypodermic holder adapted to receive a disposable ampoule, said holder comprising:
   (a) a plunger element,
   (b) a hollow body for receiving the disposable ampoule, and
   (c) optionally, a cammimg element, the improvement being wherein the body comprises
      (a) a semi-cylindrical hollow frame comprising
         a distal end portion having lugs on its outside surface radially positioned to pivotably engage a forwardly pivotable element, and
         a projecting means on its inside surface to position the disposable ampoule; and
         a proximal end portion having a short cylindrical section having a bore therethrough for receiving the plunger and optional camming elements,
         a finger gripping means and
         a projecting lug on its inside surface to position the the disposable ampoule and optionally engage the camming means; and
      (b) the forwardly pivotable element comprising
         two side walls joined by an extended connecting wall;
         each side wall having a slot for inserting a lug of the distal end portion of the frame upon which the element can pivot;
         the connecting wall having a radial portion curved to continue the cylindrical shape of the frame when the forwardly pivotable element is in a closed position and
         a curved opening at the distal end to continue the cylindrical shape of the frame when the pivotable element is in an open position, wherethrough the disposable ampoules can be ejected in an axial direction, and projections on the inside surface at the proximal end of the curved rounded opening, said projections being parallel to the side walls and adapted to engage and position the disposable ampoule when the pivotable element is in a closed position.

2. An improvement in an hypodermic holder adapted to receive a disposable ampoule, said holder comprising:
   (a) a plunger element, and
   (b) a hollow body for receiving the disposable ampoule, the improvement being wherein the body comprises
      (a) a semi-cylindrical hollow frame comprising
         a distal end portion having lugs on its outside surface radially positioned to pivotably engage a forwardly pivotable element, and
         a projecting means on its inside surface to position the disposable ampoule; and
         a proximal end portion having a short cylindrical section having a bore therethrough for receiving the plunger element,
         a finger gripping means and a projecting lug on its inside surface to position the disposable ampoule; and
      (b) the forwardly pivotable element comprising
         two side walls joined by an extended connecting wall;
         the distal end of each side wall having a slot for inserting a lug of the distal end portion of the frame upon which the element can pivot;
         the connecting wall having
         a radial curved portion sized to continue cylindrical shape of the frame when the forward pivotable element is in a closed position and
         a curved opening at the distal end thereof shaped to continue the cylindrical shape of the frame when the pivotable element is in an open position, wherethrough the disposable ampoule can be ejected in an axial direction, and
         projections on the inside surface at the proximal end of the curved opening, said projections being parallel to the side walls and adapted to engage and position the disposable ampoule when the pivotable element is in a closed position.

3. The holder of claim 1, further comprising an axially movable camming element rotatable about its longitudinal axis within the cylindrical head of said frame portion and engageable with an associated ampoule to securely immobilize the ampoule within the frame portion of the syringe holder.

4. The holder of claim 3, wherein
   said camming element comprising
      a barrel portion being sized to rotate and translate within said cylindrical head;
      a handle portion,
      a helical groove on the outer surface of said barrel portion,
      a bore there through, and
      a ramp means for permitting said lug to access said helical groove connecting said helical groove with the distal end surface of said camming element.

5. The holder of claim 1, wherein said plunger element has a rod portion on its distal end means for engaging a piston of an associated ampoule, said rod portion and piston engaging means being axially and slidably receivable within said bore of said camming element.

6. The holder of claim 2, wherein said plunger element has a too portion on its distal end means for engaging a piston of an associated ampoule, said rod portion and piston engaging means being axially and slidably receivable within said bore of said frame.

7. The syringe holder of claim 1 wherein said frame portion, said pivotable element, said optional camming element and said plunger element are fabricated of plastic.

* * * * *